(12) United States Patent
Xu et al.

(10) Patent No.: US 9,695,096 B2
(45) Date of Patent: Jul. 4, 2017

(54) MORE ENERGY EFFICIENT C5 HYDROGENATION PROCESS

(75) Inventors: Yongqiang Xu, Pasadena, TX (US); Gary G. Podrebarac, Pasadena, TX (US)

(73) Assignee: Lummus Technology Inc., Bloomfield, NJ (US)

( * ) Notice: Subject to any disclaimer, the term of this patent is extended or adjusted under 35 U.S.C. 154(b) by 0 days.

(21) Appl. No.: 13/547,164

(22) Filed: Jul. 12, 2012

(65) Prior Publication Data
US 2014/0018584 A1 Jan. 16, 2014

(51) Int. Cl.
| | |
|---|---|
| C07C 5/08 | (2006.01) |
| C07C 5/03 | (2006.01) |
| C07C 5/09 | (2006.01) |
| C07C 5/05 | (2006.01) |
| C07C 7/167 | (2006.01) |
| C07C 6/04 | (2006.01) |
| C07C 7/163 | (2006.01) |

(52) U.S. Cl.
CPC ............ *C07C 7/167* (2013.01); *C07C 6/04* (2013.01); *C07C 7/163* (2013.01); *Y02P 20/127* (2015.11); *Y02P 20/142* (2015.11)

(58) Field of Classification Search
USPC ....................................................... 585/251
See application file for complete search history.

(56) References Cited

U.S. PATENT DOCUMENTS

| | | | |
|---|---|---|---|
| 5,698,760 A * | 12/1997 | Kelly | 585/643 |
| 5,847,249 A * | 12/1998 | Maraschino | 585/259 |
| 5,877,363 A | 3/1999 | Gildert et al. | |
| 6,495,732 B1 | 12/2002 | Hearn et al. | |
| 6,884,917 B1 * | 4/2005 | Coleman | 585/643 |
| 8,389,789 B2 | 3/2013 | Gartside et al. | |
| 2003/0233017 A1 | 12/2003 | Gelbein et al. | |
| 2005/0222475 A1 | 10/2005 | Duplan et al. | |

(Continued)

FOREIGN PATENT DOCUMENTS

| | | |
|---|---|---|
| EP | 0556025 A1 | 8/1993 |
| WO | 2010/107675 A2 | 9/2010 |

OTHER PUBLICATIONS

International Search Report and Written Opinion issued Oct. 22, 2013 in corresponding International application No. PCT/US2013/049925 (14 pages).

(Continued)

*Primary Examiner* — In Suk Bullock
*Assistant Examiner* — Youngsul Jeong
(74) *Attorney, Agent, or Firm* — Osha Liang LLP (57) ABSTRACT

A process for the conversion of linear pentenes to propylene is disclosed. The process may include feeding hydrogen and a C5-olefin containing stream comprising linear pentenes, dienes, acetylenes, and cyclopentene to a catalytic distillation reactor system. Concurrently in the catalytic distillation reactor system, the acetylenes and dienes may be hydrogenated and the C5-olefin containing stream may be fractionated, thereby recovering an overheads fraction comprising the linear pentenes, a side draw fraction comprising the cyclopentene, and a bottoms fraction. In some embodiments, at least a portion of the overheads fraction may then be fed to a metathesis reactor for converting the linear pentenes to propylene.

12 Claims, 5 Drawing Sheets

(56) References Cited

U.S. PATENT DOCUMENTS

2010/0056839 A1    3/2010  Ramachandran et al.
2010/0240937 A1*   9/2010  Gartside et al. .............. 585/315
2011/0021858 A1    1/2011  Ramachandran et al.

OTHER PUBLICATIONS

First Office Action (with translation) issued Aug. 5, 2015 in corresponding Chinese application No. 201380037139.7 (19 pages).
Invitation to Respond to Written Opinion issued Oct. 1, 2015 in corresponding Singapore application No. 11201500162V (6 pages).
Office Action issued Dec. 7, 2015 in corresponding Korean application No. 10-2015-7001038 (w/translation) (9 pages).
Extended European Search Report dated Jan. 26, 2016 in corresponding European application No. 13817260.6 (6 pages).

* cited by examiner

MORE ENERGY EFFICIENT C5 HYDROGENATION PROCESS

FIELD OF THE DISCLOSURE

Embodiments disclosed herein relate generally to an energy efficient process to produce linear C5 olefins with a very low level of cyclopentene. The linear C5 olefins may be suitable for use in a downstream metathesis unit for the production of propylene, for example.

BACKGROUND

Crude streams for the commercial production of olefins contain various compounds as impurities. Acetylenic and diene impurities need to be removed from the streams to produce acceptable quality olefin products. To produce olefins such as ethylene, propylene, butadiene, pentenes and the like, acetylenic impurities such as acetylene, methyl acetylene, vinyl acetylene, ethyl acetylene, 2-methyl-1-buten-3-yne and the like, as well as diene compounds, such as butadiene, propadiene, and the like, in various crude mixed C2-C5 streams need to be removed with minimum loss of useful materials such as ethylene, propylene, butenes, pentenes, and the like in the feed streams. The preferred technique for the purification in commercial practice is the selective hydrogenation of acetylenic and diene compounds over hydrogenation catalysts.

Crude C5 olefin-containing streams may include various dienes and acetylenes, which often must be removed before use of the C5 olefin-containing stream in downstream processing units, such s a downstream metathesis unit. In addition to the need to remove dienes and acetylenes, which produce coke and shorten metathesis catalyst run length, cyclopentene must also be removed from the C5 feed to a very low level, such as less than 0.5 wt. %, as cyclopentene may undergo undesirable ring-opening metathesis polymerization in the downstream metathesis unit. The very close boiling points of linear C5 olefins and cylcopentene, however, require that a very high reflux ratio be used during fractionation or catalytic distillation to sufficiently separate the cyclopentene, recovered in the bottoms fraction, from the linear pentenes, recovered in the overheads fraction.

SUMMARY OF THE CLAIMED EMBODIMENTS

It has been found that, for a catalytic distillation reactor system, concurrently selectively hydrogenating the acetylenic and diene impurities and separating the linear pentenes from cyclopentene, withdrawing a side draw fraction from the column at a location where cyclopentene is at a high concentration may greatly improve separation efficiency and/or reduce operating costs In one aspect, embodiments disclosed herein relate to a process for the selective hydrogenation of acetylenes and dienes in a C5 hydrocarbon stream. The process may include feeding hydrogen and a C5-olefin containing stream comprising linear pentenes, dienes, acetylenes, and cyclopentene to a catalytic distillation reactor system. Concurrently in the catalytic distillation reactor system, the acetylenes and dienes may be hydrogenated and the C5-olefin containing stream may be fractionated, thereby recovering an overheads fraction comprising the linear pentenes, a side draw fraction comprising the cyclopentene, and a bottoms fraction.

In another aspect, embodiments disclosed herein relate to a process for the conversion of linear pentenes to propylene. The process may include feeding hydrogen and a C5-olefin containing stream comprising linear pentenes, dienes, acetylenes, and cyclopentene to a catalytic distillation reactor system. Concurrently in the catalytic distillation reactor system, the acetylenes and dienes may be hydrogenated and the the C5-olefin containing stream may be fractionated, thereby recovering an overheads fraction comprising the linear pentenes, a side draw fraction comprising the cyclopentene, and a bottoms fraction. At least a portion of the overheads fraction may then be fed to a metathesis reactor for converting the linear pentenes to propylene.

In another aspect, embodiments disclosed herein relate to a system for the selective hydrogenation of acetylenes and dienes in a C5 hydrocarbon stream. The system may include: one or more flow lines for feeding hydrogen and a C5-olefin containing stream comprising linear pentenes, dienes, acetylenes, and cyclopentene to a catalytic distillation reactor system; the catalytic distillation reactor system, for concurrently: hydrogenating the acetylenes and dienes; and fractionating the C5-olefin containing stream; an overheads system fluidly connected to the catalytic distillation reactor system for recovering an overheads fraction comprising the linear pentenes; a flow line for recovering a side draw fraction comprising the cyclopentene from the catalytic distillation reactor system; and a bottoms system for recovering a bottoms fraction from the catalytic distillation reactor system.

Other aspects and advantages will be apparent from the following description and the appended claims.

DETAILED DESCRIPTION

In one aspect, embodiments herein relate to an energy efficient process to produce linear C5 olefins with a very low level of cyclopentene. The linear C5 olefins may be suitable for use in a downstream metathesis unit for the production of propylene, for example.

Within the scope of this application, the expression "catalytic distillation reactor system" denotes an apparatus in which the catalytic reaction and the separation of the products take place at least partially simultaneously. The apparatus may comprise a conventional catalytic distillation column reactor, where the reaction and distillation are concurrently taking place at boiling point conditions, or a distillation column combined with at least one side reactor, where the side reactor may be operated as a liquid phase reactor or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

Feed streams according to embodiments disclosed herein may include various refinery stream containing C5 olefins and various dienes and acetylenic compounds. For example, a C4-C6 cut, a C5 cut, a C5-C6 cut or other various C5 olefin-containing mixtures may be used. In some embodiments, the feed stream is a C5 fraction containing linear pentenes, cyclopentene, as well as diene and/or acetylenic compounds. Mixed pentene feedstocks useful in embodiments disclosed herein may include linear pentenes and isopentenes. Mixed pentene feedstocks may also include various other hydrocarbon components, including C4 to C6 paraffins and olefins. In some embodiments, the mixed pentene feedstock may be a C5 hydrocarbon fraction from a catalytic or steam cracker, where the C5 fraction may include linear pentenes, isopentene, n-pentanes, and iso-pentenes.

Figure 1:
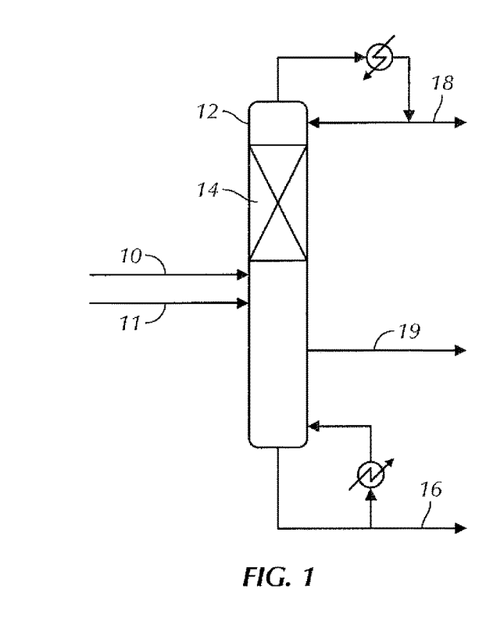
FIG. 1 is a simplified process flow diagram of a process for selectively hydrogenating acetylenes and dienes in a crude C5 stream according to embodiments disclosed herein.

FIG. 1 illustrates a simplified process flow diagram of a process for selectively hydrogenating acetylenes and dienes in a crude C5 stream according to embodiments disclosed herein. A C5 olefin-containing feed and hydrogen are fed via flow lines 10 and 11, respectively, to a catalytic distillation reactor system 12 including one or more hydrogenation reaction zones. As illustrated in FIG. 1, catalytic distillation reactor system 12 includes a reaction zone 14 located above the feed location.

In catalytic distillation reactor system 12, the C5 olefin-containing feed is concurrently fractionated and selectively hydrogenated. The lighter components in the C5 olefin-containing feed traverse up the column, where any acetylenes and dienes may be reacted with hydrogen to produce additional olefins and paraffins, before being recovered as an overheads fraction 18. The heavier components in the C5 olefin-containing feed traversed down the column and are fractionated to produce a cyclopentene-rich side draw 19 and a bottoms fraction 16.

Figure 3:
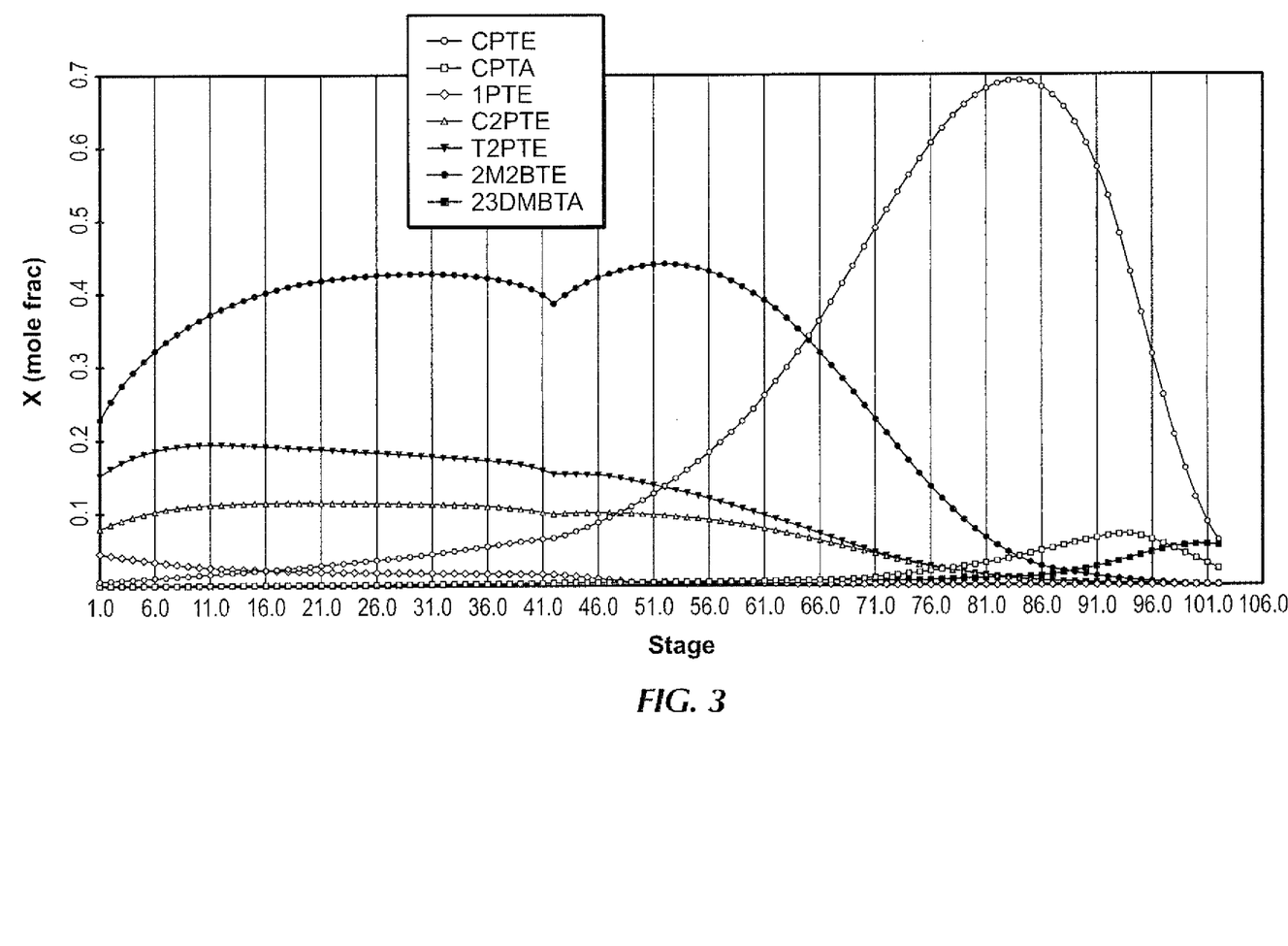
FIG. 3 presents simulation results for a comparative column, without a side draw.
Figure 4:
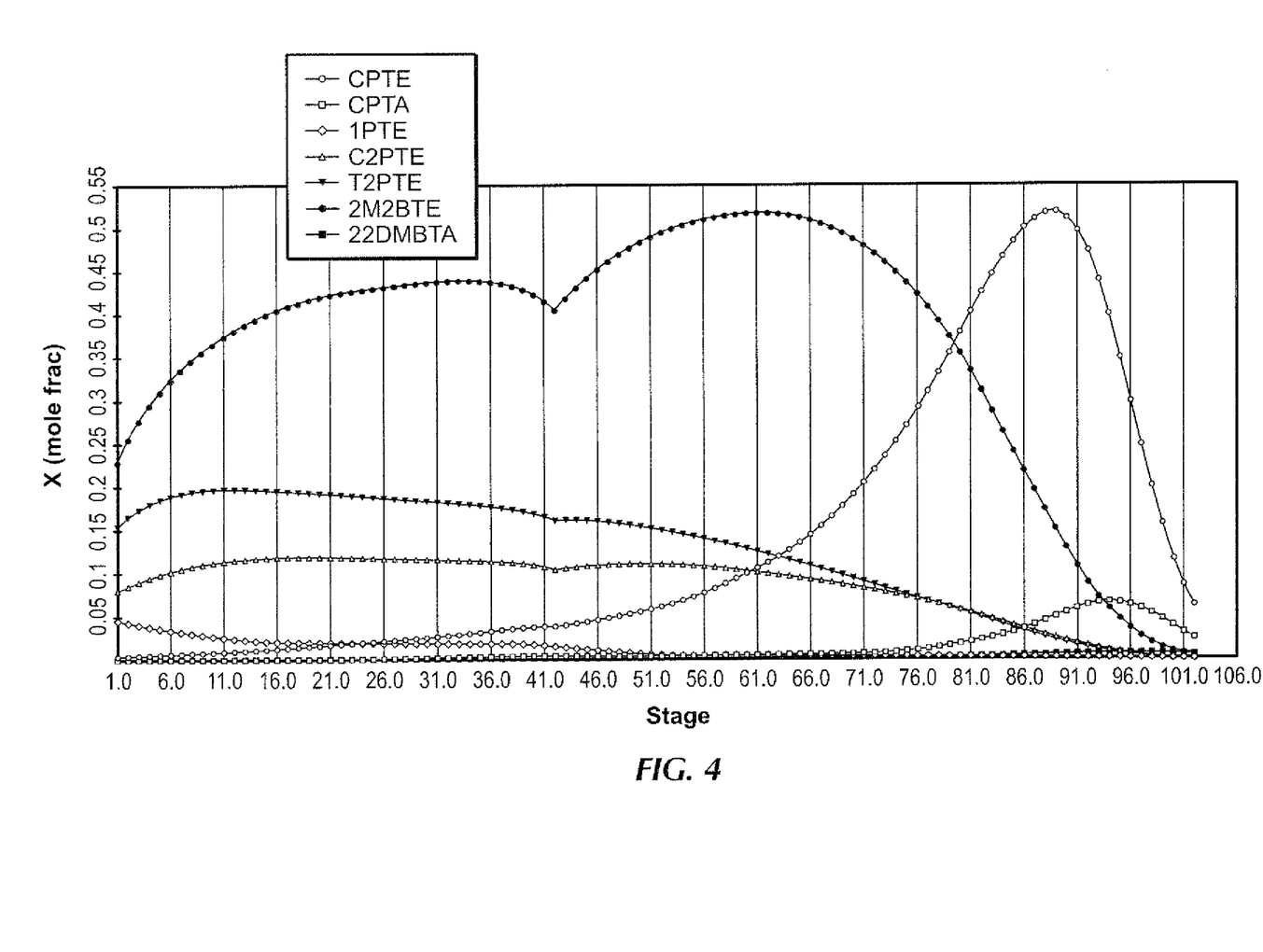
FIGS. 4-6 present simulation results for a catalytic distillation reactor system including a side draw for selectively hydrogenating acetylenes and dienes in crude C5 stream according to embodiments disclosed herein.
Figure 5:
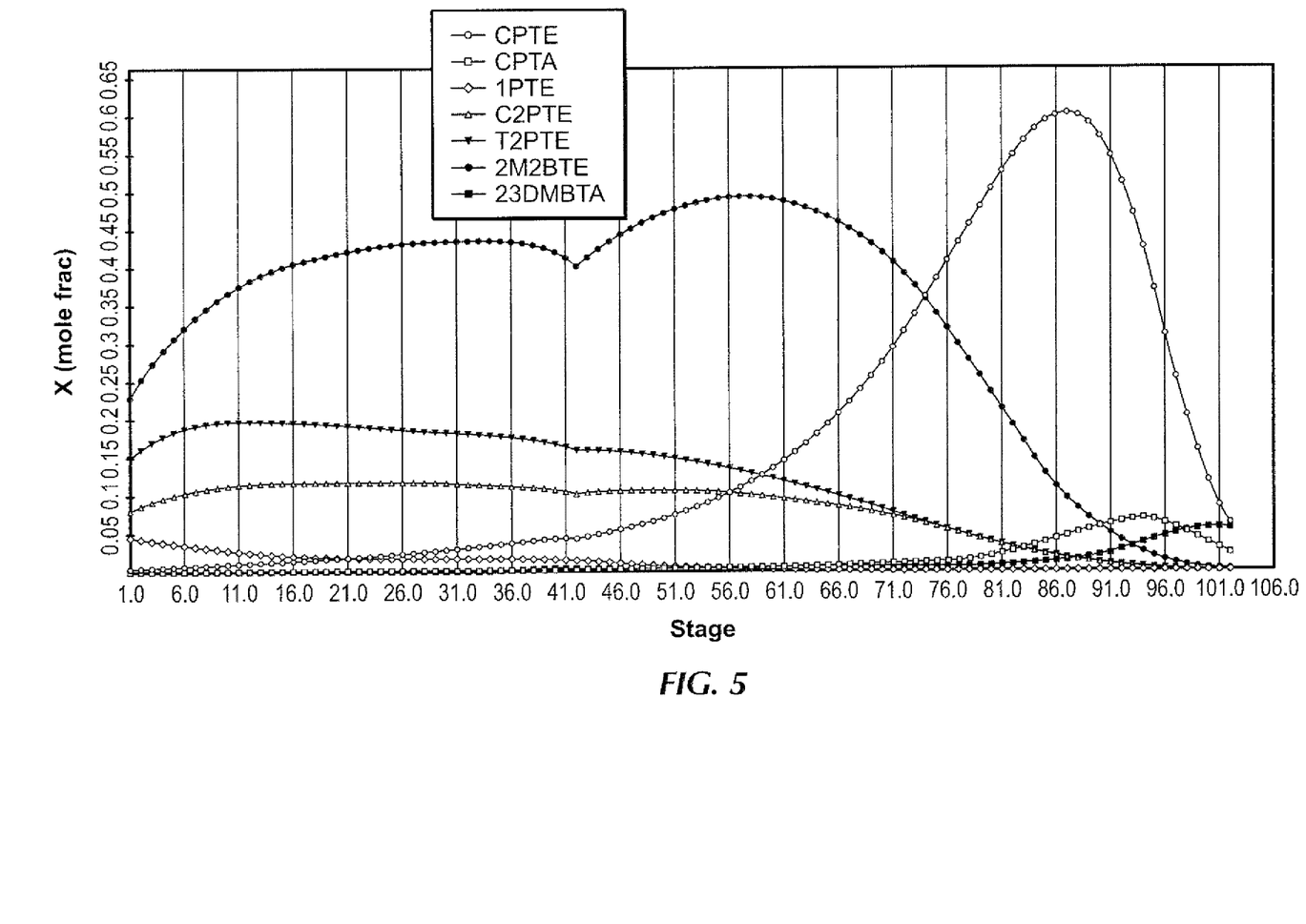
Figure 6:
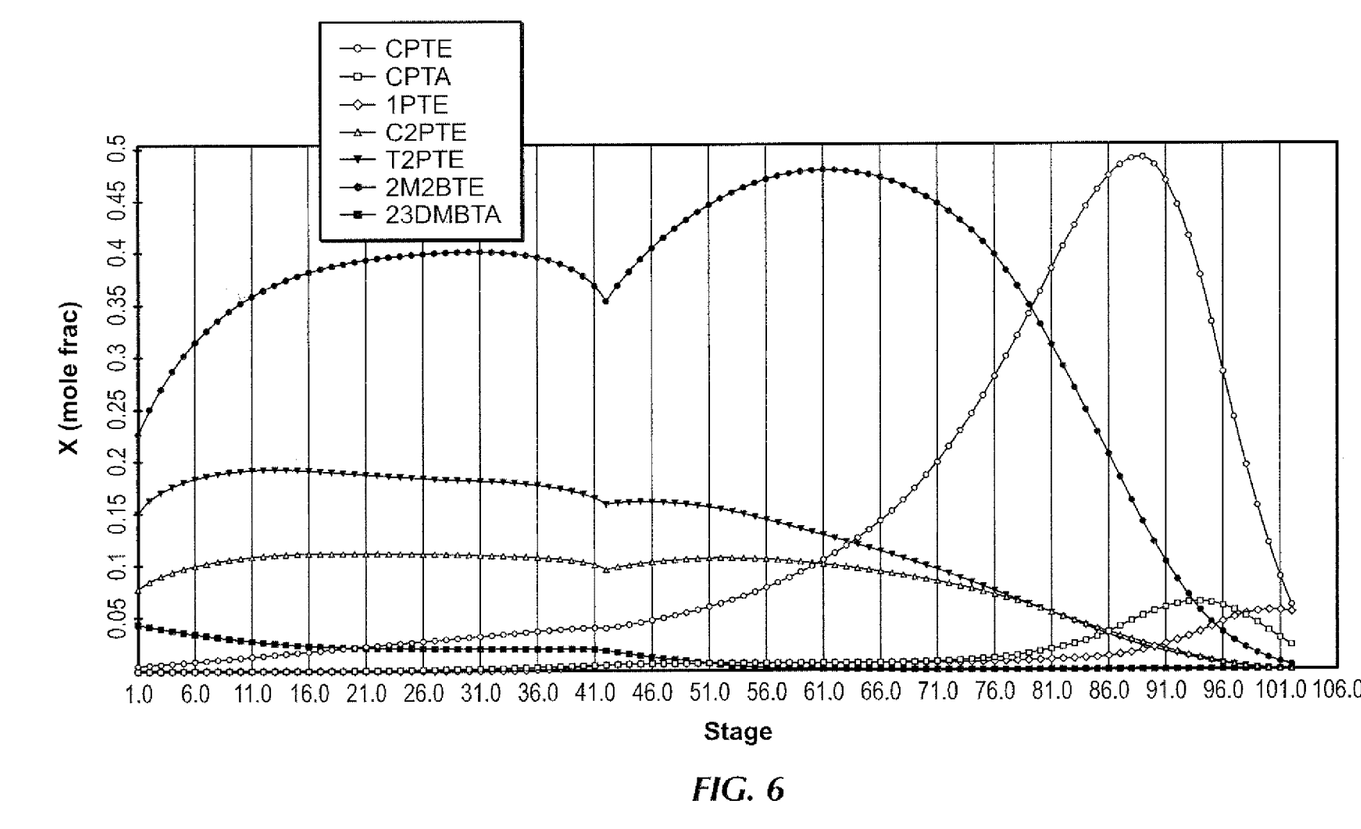

Side draw 19 is located intermediate the feed elevation and the bottom draw. In some embodiments, the side draw may be located proximate an elevation at which the concentration of cyclopentene is elevated within the column, relative to the feed. In some embodiments, the side draw is located below the feed stage and proximate an elevation of maximum cylcopentene concentration determined as if the side draw were not present. As used herein, "proximate an elevation" means within a few distillation stages, such as within about 10 or 15 stages for a column having 100 stages, for example, where the term "stage" or "distillation stage" refers to actual distillation trays or an equivalent (theoretical or otherwise) height of packing, for example. As an example, for a given C5-olefin containing feed, it may be determined, such as via simulation or sampling, that the cyclopentene is at a peak concentration within the column at stage 80; the sidedraw may thus be located between stages 70 and 90, for example. As a further example, FIG. 3 illustrates a composition profile within a column, showing peak cyclopentene concentration proximate stages 88 and 89; the side draw may be located between stages 85 and 90, for example.

Withdrawing a cyclopentene-rich stream as a side draw from the column may enhance separation efficiency, decreasing the overall traffic of cyclopentene within the column. As a result, it may be possible to decrease the concentration of cyclopentene in the overheads fraction 18 as compared to a column without a side draw under similar operating conditions (i.e., similar overheads pressure, feed rate, reboiler duty, and reflux ratio). Alternatively, the reduction in cyclopentene traffic within the column may allow one to reduce overhead condenser and/or reboiler duties, as compared to a column without a side draw, while achieving a similar concentration of cyclopentene in the overheads fraction; in some embodiments, overhead condenser and reboiler duties may be reduced by as much as 20%, 25%, 30% or greater while achieving a similar concentration of cyclopentene in the overheads fraction.

The side draw stream may be relatively small even while achieving the above noted efficiencies. In some embodiments, the side draw may be less than about 10 mol % of the total feed. In other embodiments, a ratio of the side draw rate to the feed rate (mol side draw/mol feed) may be in the range from about 0.001 to about 0.01, such as in the range from about 0.002 to about 0.005.

Depending upon the location of the side draw, the side draw may withdraw linear olefins as well as dienes and acetylenes from the column. However, where the side draw is located relatively remote from the feed location, the loss of linear olefins through the side draw may be relatively small, such as less than 0.01% to 0.1%, such as about 0.02% to about 0.03%. These negligible losses in linear olefins are relatively insignificant as compared to the gains in separation efficiency or decreases in duties that may be achieved via use of a side draw. Thus, in some embodiments, the side draw may be (a) located below the feed stage, and (b) proximate an elevation of (i) maximum cylcopentene concentration determined as if the side draw were not present and (ii) a low or minimum concentration of linear olefins.

Figure 2:
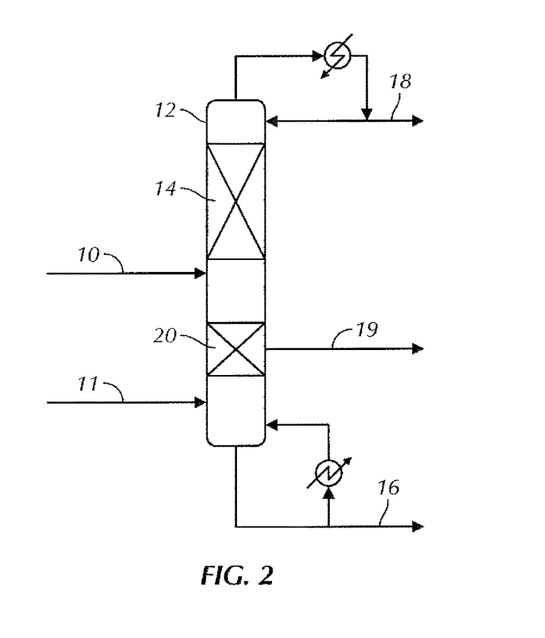
FIG. 2 is a simplified process flow diagram of a process for selectively hydrogenating acetylenes and dienes in a crude C5 stream according to embodiments disclosed herein.

As noted above, dienes and acetylenes may be withdrawn from the column along with the cyclopentene in the side draw. This may be due to column dynamics, as well as a result of the particular feedstock, which may include heavier acetylenic and diene compounds that do not boil up into the hydrogenation reaction zone. As the cyclopentene side draw may be useful as a feedstock in various downstream operations, it may be desirable to reduce or eliminate acetylenes and dienes that may be withdrawn from the column in the side draw. Location of the feed proximate or within the hydrogenation reaction zone may be used to reduce the concentration of acetylenes and dienes in side draw 19. Alternatively, a second hydrogenation reaction zone 20 may be used in the column, intermediate the feed point and side draw location or proximate the side draw location, such as illustrated in FIG. 2, where like numerals represent like parts. Use of a second hydrogenation reaction zone may effectively hydrogenate acetylenes and dienes traversing downward through the column, providing for a cyclopentene-rich side draw product substantially free of acetylenes and dienes. As used herein, substantially free of dienes and acetylenes is defined as being less than about 0.5 wt. % dienes and acetylenes.

Catalysts useful in the hydrogenation reaction zone(s) may include Group 8 metals, such as cobalt, nickel, palladium, or platinum, alone or in combination, and/or Group 1B metals, such as copper, and/or other metals, such as a Group 5A or Group 6A metals, such as molybdenum or tungsten, on a suitable support, such as alumina, silica, titania, silica-alumina, titania-alumina, titania-zirconia, or the like. Normally the catalytic metals are provided as the oxides of the metals supported on extrudates or spheres. The metals may be reduced to the hydride form or other active states, if necessary, prior to use by exposure to hydrogen, for example.

The particular catalyst(s) and operating conditions in the hydrogenation reaction zone(s) may depend upon the particular C5-olefing containing feed(s) used, the overall flow scheme (i.e., use of or lack of guard beds, etc.), the desired conversion and selectivity, and the tolerance in end products for any isomerization that may occur under hydrogenation conditions, among other variables. Typical hydrogenation reaction zone operating conditions include temperatures in the range from 30° C. to 500° C. and pressures ranging from 1 to 100 bar.

In some embodiments, hydrogenation reaction zone temperatures may range from about 30° C. to about 300° C. In other embodiments, hydrogenation reaction zone temperatures may range from about 40° C. to about 250° C.; from about 50° C. to about 200° C. in other embodiments; and from about 75° C. to about 175° C. in yet other embodiments. In embodiments where an upper and lower reaction zone are provided, the temperature in the lower bed will be greater than that of the upper bed, both of which are generally captured by the above ranges. Overheads and bottoms temperatures of the column may be greater than or less than the temperatures indicated above, the bottoms operating at a temperature proximate the boiling range of the heavier feed components at column pressure, and the overheads operating at a temperature proximate the boiling range of the lighter feed components and reaction products at column pressure.

In some embodiments, distillation column reaction system may operate at an overhead pressure in the range from about 1 bar to about 50 bar (absolute). In other embodiments, hydrogenation reactor pressures may range from about 2 bar to about 30 bar; from about 3 bar to about 20 bar in other embodiments; and from about 5 to about 10 bar, such as about 7 to 9 bar, in yet other embodiments.

Following selective hydrogenation of the acetylenic and diene compounds and separation of the linear pentenes from cyclopentene, the resulting C5 olefin-containing product may be fed to a metathesis reactor for the production of propylene. For example, the linear pentenes may be reacted with ethylene in the presence of a metathesis catalyst or a combined metathesis/isomerization catalyst to produce propylene. When linear pentenes are fed to a conventional metathesis reactor, the following reactions may occur:
(a) 1-pentene-→2-pentene (Isomerization);
(b) 2-pentene+ethylene-→1-butene+propylene (Metathesis);
(c) 1-butene-→2-butene (Isomerization);
(d) 2-butene+ethylene-→2 propylene (Metathesis).
1-Pentene is isomerized to 2-pentene. The metathesis reaction of 1-pentene with ethylene is non-productive (products are same as reactants). The overall linear C5 olefin reaction can thus be shown as:
1 linear pentene+2 ethylene-→3 propylene.

The metathesis reaction products, including unreacted ethylene, propylene, butenes, and unreacted pentenes may then be recovered and forwarded to a separation zone, which may include one or more distillation columns and/or extractive distillation columns for separating the metathesis reactor effluent into various desired fractions, which may include an ethylene fraction, a propylene fraction, a butene and/or pentene fraction, and a heavies fraction. The ethylene fraction and butene/pentene fraction(s) may be recycled to the metathesis reaction zone for continued production of propylene.

Catalysts useful in the metathesis reactor may include any known metathesis catalyst, including oxides of Group VIA and Group VIIA metals on supports. Catalyst supports can be of any type and could include alumina, silica, mixtures thereof, zirconia, and zeolites. In addition to the metathesis catalyst, the catalyst contained in the metathesis reactor may include a double bond isomerization catalyst such as magnesium oxide or calcium oxide, for converting 1-butene and 1-pentene to 2-butene and 2-pentene, allowing for increased production of propylene via metathesis with ethylene. In some embodiments, the catalyst may include a promoter to reduce acidity; for example, an alkali metal (sodium, potassium or lithium), cesium, a rare earth, etc. In some embodiments, the metathesis or mixed metathesis/double bond isomerization catalyst may include those described in U.S. 20110021858 or U.S. 20100056839, for example.

The metathesis reactor may operate at a pressure between 1 and 40 bar in some embodiments, and between 5 and 15 bar in other embodiments. The metathesis reactor may be operated such that the reaction temperature is within the range from about 50° C. to about 600° C.; within the range from about 200° C. to about 450° C. in other embodiments; and from about 250° C. to about 400° C. in yet other embodiments. The metathesis reaction may be performed at a weight hourly space velocity (WHSV) in the range from about 3 to about 200 in some embodiments, and from about 6 to about 40 in other embodiments. The reaction may be carried out in the liquid phase or the gas phase, depending on structure and molecular weight of the olefin(s), by contacting the olefin(s) with the metathesis catalyst. If the reaction is carried out in the liquid phase, solvents or diluents for the reaction can be used, such as aliphatic saturated hydrocarbons, e.g., pentanes, hexanes, cyclohexanes, dodecanes, and aromatic hydrocarbons such as benzene and toluene are suitable. If the reaction is carried out in the gaseous phase, diluents such as saturated aliphatic hydrocarbons, for example, methane, ethane, and/or substantially inert gases, such as nitrogen and argon, may be present. For high product yield, the reaction may be conducted in the absence of significant amounts of deactivating materials such as water and oxygen.

EXAMPLES

Simulations were conducted to compare the performance of a catalytic distillation reactor system for selectively hydrogenating a C5 feed stream with and without a side draw. The C5 feed composition is shown in Table 1. Simulations were carried out in ASPEN PLUS 7.2 (Aspen Technology, Inc., Burlington, Mass.). Simulations for columns with a side draw were performed with the column configuration as shown in FIG. 1. Simulation results are compared in Table 2.

It can be seen from Table 2 and the FIGS. 3-6 that with the same cyclopentene concentration in the distillate (0.5 wt %), the reboiler duty can be significantly decreased from 31,571 btu/h (Case 1) to 23,498 btu/h (Case 4) by taking a small side draw enriched in cyclopentene. Interestingly the total linear C5 olefin loss through the side draw is negligible (0.08 wt %). If using the same reflux ratio and reboiler duty as shown in Cases 2 and 3, an overhead product with a much less concentration of cyclopentene is produced by taking a small sidestream enriched in cyclopentene from the column.

TABLE 1

C5 Feed Composition (wt. %)

| Component | Wt. % |
|---|---|
| 1-butene | 0.0525 |
| isobutene | 0.5477 |
| n-butane | 0.1405 |
| 1,4-pentadiene | 0.0064 |
| cis 1,3-pentadiene | 0.0775 |
| 2-methyl 1-butene | 5.0019 |
| 4-methyl 1-pentene | 0.4733 |
| cyclopentene | 1.8741 |
| n-pentane | 3.6866 |
| 3-methyl 1,3-pentadiene | 0.0335 |
| trans 1,3-hexadiene | 0.1525 |
| 2,3-dimethyl 1-butene | 0.5611 |
| 2-methyl 2-pentene | 2.1323 |
| cis 2-hexene | 0.9268 |
| cis 4-methyl 2-pentene | 0.4486 |
| trans 3-hexene | 0.8618 |
| 2,2-dimethylbutane | 0.1158 |
| n-hexane | 1.2040 |
| 2,2,3-trimethylbutane | 0.0360 |
| Toluene | 0.0463 |
| 3-methyl 1-butene | 0.7513 |
| trans 2-butene | 0.6300 |
| cyclopentadiene | 0.0170 |
| 1,5-hexadiene | 0.0119 |
| trans 1,3-pentadiene | 0.1408 |
| 2-methyl 2-butene | 14.1153 |
| cis 2-pentene | 4.9555 |
| trans 2-pentene | 9.4822 |
| 1,4-hexadiene | 0.0053 |
| 3-methyl 1,4-pentadiene | 0.0710 |
| 1-hexene | 0.4480 |
| 2-ethyl 1-butene | 0.0300 |
| 3,3-dimethyl 1-butene | 0.1055 |
| cis 3-hexene | 0.2812 |
| methyl cylcopentane | 1.3342 |
| trans 3-methyl 2-pentene | 1.3668 |
| 2,3-dimethylbutane | 2.0282 |
| 2,4-dimethyl 1-pentene | 0.0243 |
| 2,4-dimethylpentane | 0.3495 |
| heavies | 0.3828 |
| cis 2-butene | 0.5753 |
| Isobutane | 0.0290 |
| 1,2-pentadiene | 0.0150 |
| 2-methyl 1,3-butadiene | 0.1105 |
| 1-pentene | 2.8576 |
| 3-methyl 1-pentene | 0.6446 |
| cyclopentane | 0.6256 |
| isopentane | 20.6196 |
| 2-methyl 1,4-pentadiene | 0.0270 |
| 3-methyl cyclopentene | 0.0060 |
| 1-methyl cyclopentene | 0.4961 |
| 2-methyl 1-pentene | 1.0288 |
| 3-methyl pentane | 4.2233 |
| cis 3-methyl 2-pentene | 1.2823 |
| trans 2-hexene | 1.7921 |
| trans 4-methyl 2-pentene | 1.7264 |
| 20 methyl pentane | 8.2805 |
| 3,3-dimethyl 1-pentene | 0.0080 |
| Benzene | 0.7423 |

As can been seen from Table 1 and FIGS. 3-6, and which can be easily interpreted by one skilled in the art, "CPTE" refers to cyclopentene, "CPTA" refers to cyclopentane, "1PTE" refers to 1-pentene, "C2PTE" refers to cis-2-pentene, "T2PTE" refers to trans-2-pentene, "2M2BTE" refers to 2-methyl-2-butene, "23DMBTA" refers to 2,3-dimethylbutane, and "22DMBTA" refers to 2,2-dimethylbutane.

TABLE 2

| Simulation Conditions | | | | |
|---|---|---|---|---|
| | Case Number | | | |
| | 1 | 2 | 3 | 4 |
| Column Stages | 102 | 102 | 102 | 102 |
| C5 Feed Stage | 42 | 42 | 42 | 42 |
| Hydrogen Feed Stage | 45 | 45 | 45 | 45 |
| Reaction Zone Stages | 30-37 | 30-37 | 30-37 | 30-37 |
| Cyclopentene in Overheads (wt %) | 0.50 | 0.28 | 0.34 | 0.50 |
| Pressure (psia) | 114.7 | 114.7 | 114.7 | 114.7 |
| Reflux Ratio | 10 | 10.05 | 10.05 | 7.3 |
| Average partial pressure of hydrogen (psi) | 0.505 | 0.505 | 0.505 | 0.505 |
| Bottoms vs. Feed ratio (mol/mol) | 0.306 | 0.306 | 0.306 | 0.306 |
| Reboiler Duty (but/h) | 31571 | 31571 | 31571 | 23498 |
| Side Draw Stage | N/A | 86 | 86 | 86 |
| Side Draw vs. Feed Ratio (mol/mol) | N/A | 0.0046 | 0.0023 | 0.0023 |
| Total linear olefin loss to side draw (wt. %) | N/A | 0.16 | 0.05 | 0.08 |

As described above, embodiments disclosed herein provide an efficient process for selectively hydrogenating dienes and acetylenes in a crude C5 hydrocarbon stream. Advantageously, the use of a side draw may provide for greater separation efficiency and/or reduced operating duties as compared to catalytic distillation reactor systems without a side draw.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the selective hydrogenation of acetylenes and dienes in a C5 hydrocarbon stream, comprising:
feeding hydrogen and a C5-olefin containing stream comprising linear pentenes, dienes, acetylenes, and cyclopentene to a catalytic distillation reactor system;
concurrently in the catalytic distillation reactor system:
hydrogenating the acetylenes and dienes; and
fractionating the C5-olefin containing stream;
wherein the catalytic distillation reactor system comprises a hydrogenation reaction zone located above a feed location of the C5-olefin containing stream;
recovering an overheads fraction comprising the linear pentenes;
recovering a side draw fraction comprising the cyclopentene through a side draw, wherein the side draw is located intermediate a feed location of the C5-olefin containing stream and a bottoms draw location; and
recovering a bottoms fraction;
wherein cyclopentene in the overheads fraction is less than 0.5 wt % and linear pentenes in the side draw fraction are in a range from 0.01 wt % to 0.1 wt %.

2. The process of claim 1, wherein the side draw is located below the feed location and proximate an elevation of maximum cyclopentene concentration determined as if the side draw were not present.

3. The process of claim 1, wherein a mole ratio of a side draw rate to a feed rate of the C5-olefin containing stream is in the range from about 0.001 to about 0.01.

4. The process of claim 1, wherein a more ratio of a side draw rate to a feed rate of the C5-olefin containing stream is in the range from about 0.002 to about 0.005.

5. The process of claim 1, wherein the catalytic distillation reactor system further comprises a hydrogenation reaction zone located below a feed location of the C5-olefin containing stream and above or proximate an elevation of the side draw.

6. The process of claim 1, wherein the side draw is substantially free of acetylenes and dienes.

7. A process for the conversion of linear pentenes to propylene, comprising:
feeding hydrogen and a C5-olefin containing stream comprising linear pentenes, dienes, acetylenes, and cyclopentene to a catalytic distillation reactor system;
concurrently in the catalytic distillation reactor system:
hydrogenating the acetylenes and dienes; and
fractionating the C5-olefin containing stream;
wherein the catalytic distillation reactor system comprises a hydrogenation reaction zone located above a feed location of the C5-olefin containing stream;
recovering an overheads fraction comprising the linear pentenes;
recovering a side draw fraction comprising the cyclopentene through a side draw, wherein the side draw is located intermediate a feed location of the C5-olefin containing stream and a bottoms draw location;
recovering a bottoms fraction; and
feeding at least a portion of the overheads fraction to a metathesis reactor;
wherein cyclopentene in the overheads fraction is less than 0.5 wt % and linear pentenes in the side draw fraction are in a range from 0.01 wt % to 0.1 wt %.

8. The process of claim 7, wherein the side draw is located below the feed location and proximate an elevation of maximum cyclopentene concentration determined as if the side draw were not present.

9. The process of claim 1, wherein a more ratio of a side draw rate to a feed rate of the C5-olefin containing stream is in the range from about 0.001 to about 0.01.

10. The process of claim 1, wherein a mole ratio of a side draw rate to a feed rate of the C5-olefin containing stream is in the range from about 0.002 to about 0.005.

11. The process of claim 7, wherein the catalytic distillation reactor system further comprises a hydrogenation reaction zone located below a feed location of the C5-olefin containing stream and above or proximate an elevation of the side draw.

12. The process of claim 7, wherein the side draw is substantially free of acetylenes and dienes.

* * * * *

UNITED STATES PATENT AND TRADEMARK OFFICE
CERTIFICATE OF CORRECTION

PATENT NO. : 9,695,096 B2
APPLICATION NO. : 13/547164
DATED : July 4, 2017
INVENTOR(S) : Yongqiang Xu et al.

Page 1 of 1

It is certified that error appears in the above-identified patent and that said Letters Patent is hereby corrected as shown below:

At Column 10, Claim number 9, Line number 13, "process of claim 1," should read -- process of claim 7 --.

At Column 10, Claim number 10, Line number 16, "process of claim 1," should read -- process of claim 7 --.

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*